United States Patent [19]
Postal et al.

[11] Patent Number: 5,931,672
[45] Date of Patent: Aug. 3, 1999

[54] DRIVE MECHANISM FOR OSCILLATORY DENTAL TOOL

[76] Inventors: Robert T. Postal, 1 Pond View Dr., Glen Cove, N.Y. 11542; Michael E. Langlais, 3 Old Mishnock Highway, Coventry, R.I. 02816

[21] Appl. No.: 08/878,995

[22] Filed: Jun. 19, 1997

[51] Int. Cl.[6] ................................................ A61C 3/03
[52] U.S. Cl. .................... 433/118; 433/122; 433/125; 74/54; 74/569
[58] Field of Search ................................. 433/118, 122, 433/123, 124, 125; 74/54, 569

[56] References Cited

U.S. PATENT DOCUMENTS

| | | | |
|---|---|---|---|
| 656,124 | 8/1900 | Kinnison | 433/124 |
| 1,711,846 | 5/1929 | Heilborn . | |
| 1,982,336 | 11/1934 | Wiseman | 433/125 |
| 2,135,933 | 11/1938 | Blair | 433/122 |
| 2,400,912 | 5/1946 | Britt et al. | 433/125 |
| 3,407,503 | 10/1968 | Nealon . | |
| 3,769,707 | 11/1973 | Condon | 433/125 |
| 4,371,341 | 2/1983 | Nakanishi | 433/118 |
| 4,460,341 | 7/1984 | Nakanishi | 433/122 |
| 4,534,733 | 8/1985 | Seigneurin et al. | 433/122 |
| 5,120,220 | 6/1992 | Butler | 433/125 |
| 5,145,369 | 9/1992 | Lustig et al. | 433/118 |
| 5,340,310 | 8/1994 | Bifulk | 433/122 |
| 5,571,012 | 11/1996 | Witherby et al. . | |

*Primary Examiner*—Ralph A. Lewis
*Attorney, Agent, or Firm*—Handal & Morofsky

[57] ABSTRACT

A dental tool assembly having a driving mechanism with interengaging camming surfaces shaped for continuous contact during use. The mechanism includes a drive shaft having a drive surface and a driven shaft having a driven surface. The cam surfaces are shaped and the shafts are transversely juxtaposed with respect to each other such that the drive surface and driven surface are in continuous contact during rotation of the drive shaft to impart oscillatory rotation to the drive shaft. Specifically, the drive surface is conical and preferably has a cone axis that is at an approximately 45° angle with respect to the rotation axis of the drive shaft. The driven surface has alternating hills and valleys that are shaped for continuous engagement with the drive surface as the drive shaft rotates. Preferably a pair of juxtaposed valleys are provided with juxtaposed hills formed therebetween. Rotation of the drive shaft causes the drive surface to ride alternately along the hills and valleys, continuously in contact with the driven surface. When the drive surface moves along a valley, the driven shaft is in a rest position. When the drive surface moves along a hill, the driven shaft is rotated approximately 45° from the rest position, contact with oppositely positioned hills causing rotation in opposite directions. Oscillatory rotation is thereby imparted to the driven shaft as the drive surface alternately engages the alternating hills and alleys.

10 Claims, 4 Drawing Sheets

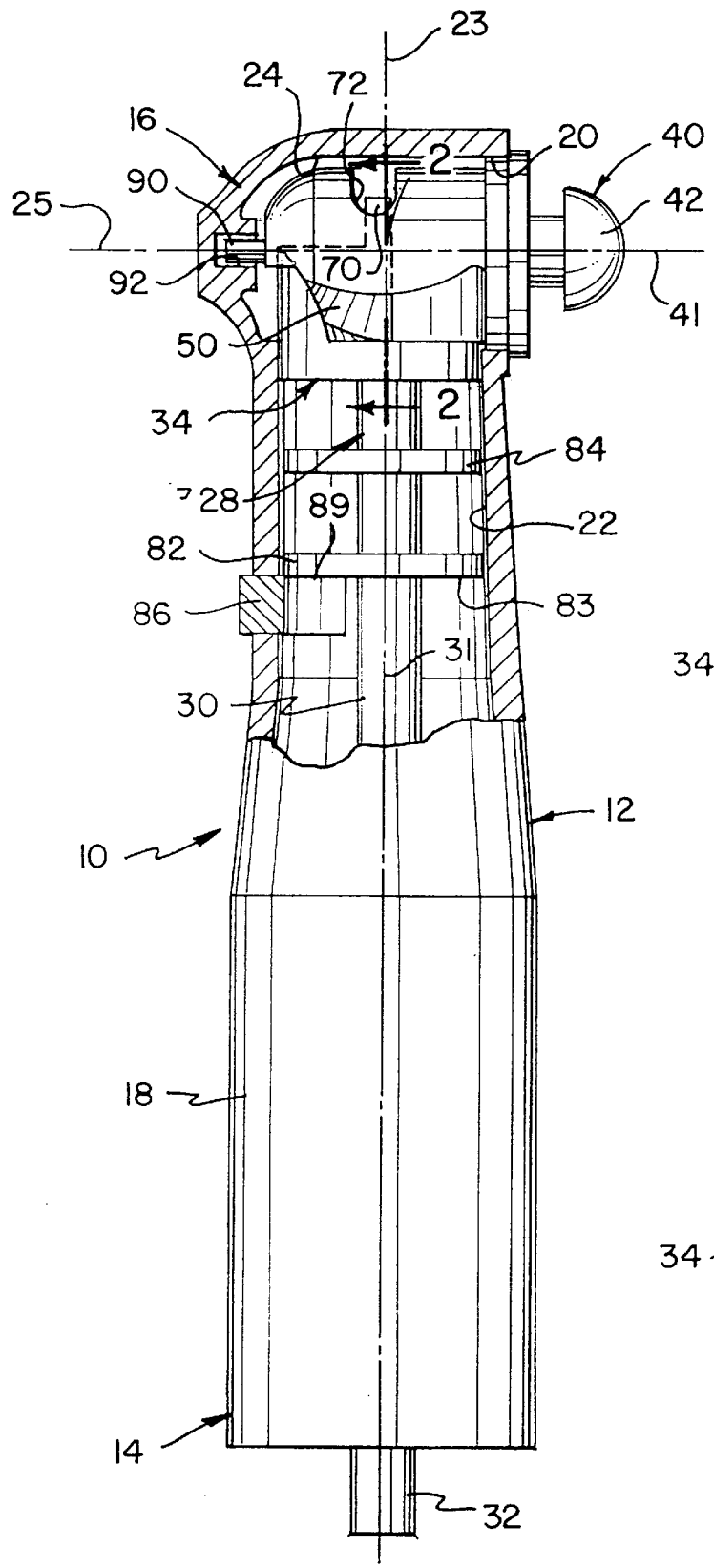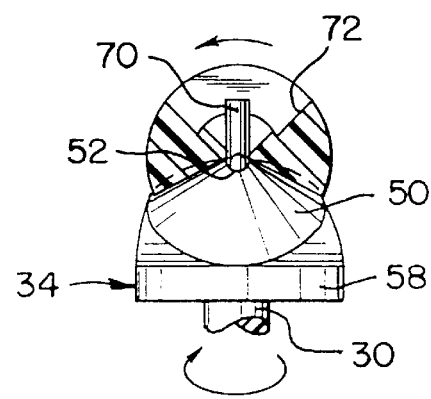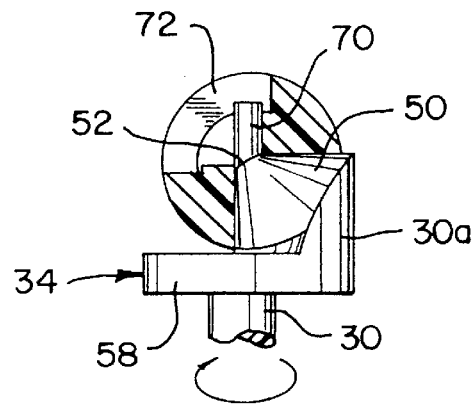

DRIVE MECHANISM FOR OSCILLATORY DENTAL TOOL

BACKGROUND OF THE INVENTION

The present invention relates to a dental tool assembly having a head that imparts oscillatory motion to a desired dental treatment device coupled to the assembly. More particularly, the present invention relates to a drive mechanism for a dental tool assembly, the drive mechanism having a rotating drive shaft that engages a first end of a driven shaft to rotate the driven shaft in an oscillatory manner. A dental tool is coupled to a second end of the driven shaft and is thereby rotationally oscillated.

Dental tool assemblies, such as prophy angles and drills, which impart an oscillatory rotary motion to a dental treatment device coupled thereto are known in the art. In particular, such assemblies typically have a driving mechanism comprising a drive shaft with a rotation axis that is perpendicular to the rotation axis of a driven shaft to which the dental treatment device is coupled. The drive shaft of prior art driving mechanisms has an element positioned eccentric to its rotation axis and extending towards the driven shaft to engage a slot in the driven shaft. Rotation of the drive shaft thus imparts an oscillatory rotation to the driven shaft.

For example, U.S. Pat. No. 1,711,846 to Heilborn shows a dental filing device having a drive shaft perpendicularly oriented with respect to a file holder. A crank pin, mounted on a crank disc on an end of the drive shaft adjacent the file holder, engages within a bore in the file holder. The crank pin is positioned on the crank disc eccentric to the rotation axis of the drive shaft. Thus, rotation of the drive shaft rotates the eccentrically positioned stud, thereby causing the file holder to rotate in an oscillatory manner.

Similarly, the dental instrument in U.S. Pat. No. 2,135,933 to Blair has a rotary drive shaft with an eccentrically positioned stud that engages within a slot of a piston to which a massage tip is coupled. Rotation of the drive shaft causes oscillatory rotation of the massage tip. Another massage tool that imparts oscillatory motion to a head spindle to which a massage cup or brush is coupled is shown in U.S. Pat. No. 4,534,733 to Seigneurin et al. In the Seigneurin Patent, the stud that engages the head spindle is mounted eccentric to the rotation axis of the drive shaft, but is inclined to extend across the rotation axis. The portion of the stud that is aligned with the rotation axis of the drive shaft is also aligned with the rotation axis of the head spindle. The dental tool shown in U.S. Pat. No. 4,460,341 to Nakanishi also has a guide pin mounted eccentric to the rotation axis of a drive shaft and engaging within a slot of a driven shaft to which a dental treatment device is coupled.

In all of the above-described dental tool assemblies, a stud or pin extends into a slot to drive the element to which the dental treatment device is coupled. Because the treatment device typically must be driven at very high speeds (e.g., the recommended speed of a standard prophy angle at approximately 6,000 rotations per minute), there is a risk of the stud or pin breaking off during use. Moreover, manufacturing of the drive shaft and driven shaft is complicated by the necessity of forming a stud and a slot that are shaped for ready, secure engagement such that rotation of the drive shaft causes oscillatory rotation of the driven shaft.

Additionally, some of the drive shafts of the above-described patents also impart reciprocatory axial motion to the driven shaft along the longitudinal shaft of the driven shaft. When such axial motion is not desired, the driven shaft should be locked with respect to the housing in which the drive shaft and driven shaft are positioned, and thus locked with respect to the rotation axis of the drive shaft. Typically, such locking is accomplished by locking the driven element with respect to the housing such as by interengagement of stepped portions and/or flanges. However, such locking imparts substantial stresses against the housing and driven shaft.

Another drawback of the above-described devices is that they are typically formed from metal and are reusable. The sterilization process necessary in order to reuse the device is typically costly and time consuming. It therefore has been desirable to provide disposable dental tool assemblies that are used only once and therefore need not be sterilized. Such tools typically are made from plastic.

Because plastics are generally not as strong as metals, the driving mechanism used in the above-described devices cannot be used because of the inherent weakness of the stud. Therefore, the driving mechanisms of disposable dental tools typically have interengaging gears, such as shown in U.S. Pat. No. 5,571,012 to Witherby et al. Because gears are used, the same reciprocatory rotary motion provided by the nondisposable tools cannot be achieved. However, such oscillating movement is desired for a number of reasons. The back and forth reciprocating motion provided by non-disposable dental tool assemblies permits greater speeds to be used and greater pressure to be applied than rotary type devices that do not oscillate, and also may massage the gums of the patient. Additionally, oscillatory movement generates less heat than a full rotational action. Moreover, the risks of hitting undercuts, cutting or tearing soft tissue, and splattering of agents applied by the treatment tool are reduced if not substantially eliminated.

SUMMARY OF THE INVENTION

It is therefore an object of the present invention to provide a disposable dental tool assembly having a driving mechanism that imparts oscillatory rotary motion to a dental treatment device mounted on the assembly.

It is a related object of the present invention to provide a driving mechanism having a drive shaft and a driven shaft each having driving surfaces shaped to engage each other and ride along each other such that rotation of the drive shaft causes oscillatory rotation of the driven shaft.

It is a further object of the present invention to provide a dental tool assembly having driving and driven elements that are stabilized with respect to each other against relative movement in a given direction.

It is another object of the present invention to provide a dental tool assembly having a drive shaft that is coupled to a driven element such that the drive shaft imparts only oscillatory motion to the driven element without also imparting axial motion to the driven element.

These and other objects of the present invention are accomplished in accordance with the principles of the present invention by providing a dental tool assembly having a rotating drive shaft that engages a driven shaft to impart oscillatory rotary motion to the driven shaft. The drive shaft and driven shaft are positioned transverse to each other. The drive shaft has a driving surface at its distal end that is shaped to engage a driven surface on a side of the driven shaft adjacent the drive shaft. Because of the manner in which the distal end is shaped, a stud or guide pin, such as used in the prior art, is no longer needed. Specifically, the driving surface is a cut-away, curved portion of an enlarged end of the drive shaft, and the driven surface is a cut-away side portion of the driven shaft. The cut-away portions of each shaft are shaped to interengage with substantially no play therebetween such that they are in continuous contact during rotation of the driving shaft. Because of the shapes of the cut-away portions, rotation of the driving shaft causes oscillatory rotation of the driven shaft.

The drive shaft and driven shaft are positioned within a housing. In order to prevent relative movement of the shafts with respect to the housing, a plurality of locking mechanisms are provided. First, the drive shaft is provided with a longitudinally extending pin aligned with the rotation axis of the drive shaft. The driven shaft is provided with a slot through which the pin is passed. The slot is shaped so that oscillatory rotation of the driven shaft is not inhibited by the pin, yet axial movement of the driven shaft along its rotation axis is prevented. Another locking mechanism for the drive shaft is provided in the form of at least one flange extending radially from the drive shaft and engaging a radially inwardly extending flange on the inner surface of the housing. The driven shaft is provided with a rearwardly positioned pin that fits within a bore in the housing to lock the driven shaft in the desired position for oscillation.

BRIEF DESCRIPTION OF THE DRAWINGS

These and other features and advantages of the present invention will be readily apparent from the following detailed description of the invention, the scope of the invention being set out in the appended claims. The detailed description will be better understood in conjunction with the accompanying drawings, wherein like reference characters represent like elements, as follows:

FIG. 1 is an elevational, partially cut-away view of a dental tool assembly formed in accordance with the principles of the present invention;

FIG. 2A is a cross-sectional view of the distal end of the dental tool assembly of FIG. 1 along line 2—2, with the driven shaft in the rest position;

FIG. 2B is a cross-sectional view of the distal end of the dental tool assembly of FIG. 1 along line 2—2 with the drive shaft rotated 90° from the position shown in FIG. 2A;

DETAILED DESCRIPTION OF THE INVENTION

Figure 3:
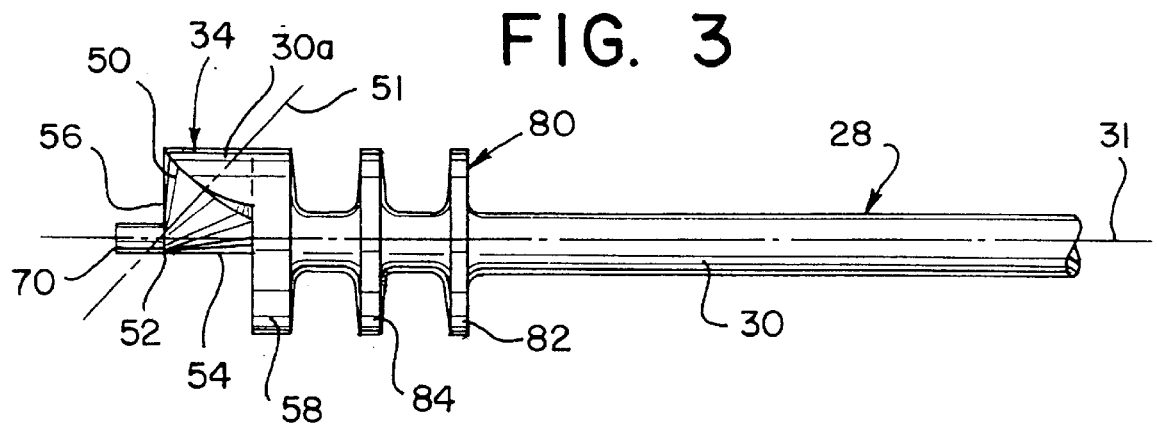
FIG. 3 is an elevational view of a drive shaft formed in accordance with the principles of the present invention.
Figure 4:
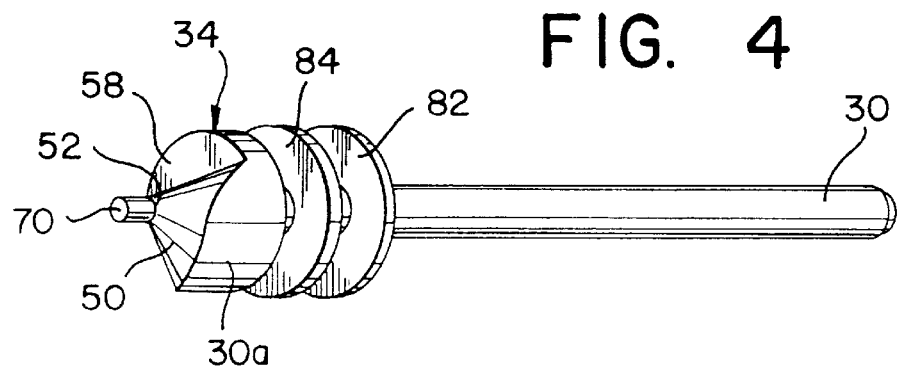
FIG. 4 is a perspective view of the drive shaft of FIG. 2.
Figure 5:
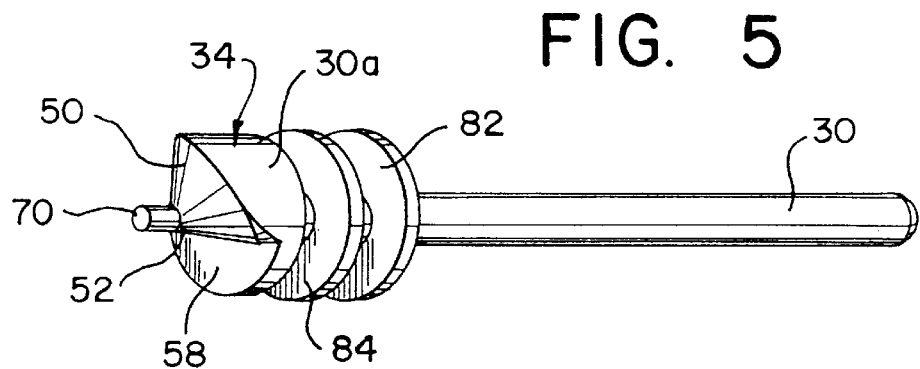
FIG. 5 is a perspective view of the drive shaft of FIGS. 3 and 4, rotated to another position.
Figure 6:
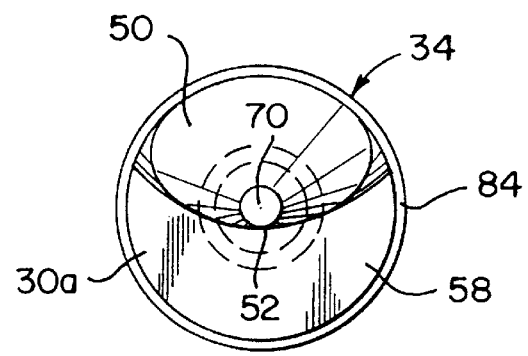
FIG. 6 is an end view of the drive shaft of FIG. 3.

A dental tool assembly 10, formed in accordance with the principles of the present invention, is shown in FIG. 1. Dental tool assembly 10 includes a housing 12 having a proximal end 14 and a distal end 16, with main body portion 18 extending therebetween. Proximal end 14 is coupled to a dental tool handpiece (not shown) known in the art. Distal end 16 has a side opening 20 at which a desired dental treatment device (not shown) is coupled. It will be understood that any dental treatment device known in the art may be used. However, the preferred embodiment of the dental tool assembly shown in the figures is a prophy angle to which a prophy cup or brush is coupled to apply prophy paste.

Housing 12 is hollow such that first and second channels 22, 24 are formed therein for housing driving mechanism 28. First, longitudinal channel 22 is formed within main body portion 18 and extends from proximal end 14 to distal end 16 along longitudinal axis 23 of main body portion 18. Second, transverse channel 24 extends across the distal end 16 of housing 12 and opens at side opening 20 of housing 12. Longitudinal axis 25 of transverse channel 24 is transverse and preferably substantially perpendicular to longitudinal axis 23 of housing 12.

Driving mechanism 28 includes a drive shaft 30 and a driven shaft 40. Drive shaft 30 is housed in first channel 22 and has a longitudinal rotation axis 31 which preferably corresponds to longitudinal axis 23 of main body portion 18. A proximal end 32 of drive shaft 30 preferably extends beyond proximal end 14 of housing 12 for connection to a rotary unit (not shown), such as a motor, for rotating drive shaft 30, as known in the art. Distal end 34 of drive shaft 30 extends toward, and preferably partially into, second channel 24. Driven shaft 40 is housed in second channel 24 and has a longitudinal rotation axis 41 which preferably corresponds to longitudinal axis 25 of transverse channel 24. Driven shaft 40 preferably has a coupling element 42 extending therefrom through side opening 20 and out of housing 12. A desired dental treatment device, selected from those known in the art such as a prophy cup or brush, may be coupled to coupling element 42.

Drive shaft 30 and driven shaft 40 have driving surfaces that are shaped to interengage each other to result in a camming action that translates rotation of drive shaft 30 into oscillatory rotation of driven shaft 40 substantially without play between the driving surfaces, as will now be described. As shown in FIGS. 2A, 2B, and 3–6, drive shaft 30 has a drive surface 50 (which functions essentially as a cam) at distal end 34. Preferably drive surface 50 has a substantially conical cam surface, with cone axis 51 being at a preferably 45° angle with respect to rotation axis 31, as may be observed in FIG. 3. The conical shape is readily appreciated with reference to FIGS. 2A, 2B, and 3–6. The tip 52 of conical drive surface 50 preferably is aligned with rotation axis 31 so that a longitudinal surface portion 54 of conical surface 50 is aligned with rotation axis 31 and a transverse surface portion 56 of conical surface 50 is substantially perpendicular, i.e., at a 90° angle, with respect to rotation axis 31 and thus with respect to longitudinal surface portion 54. As may be seen in FIGS. 2B and 3–6, conical surface 50 is formed to one side of rotation axis 31. Conical surface 50 may be formed by cutting away a portion of an enlarged region 30a of shaft 30, thus leaving a flange-like section 58 at distal end 34.

Figure 7:
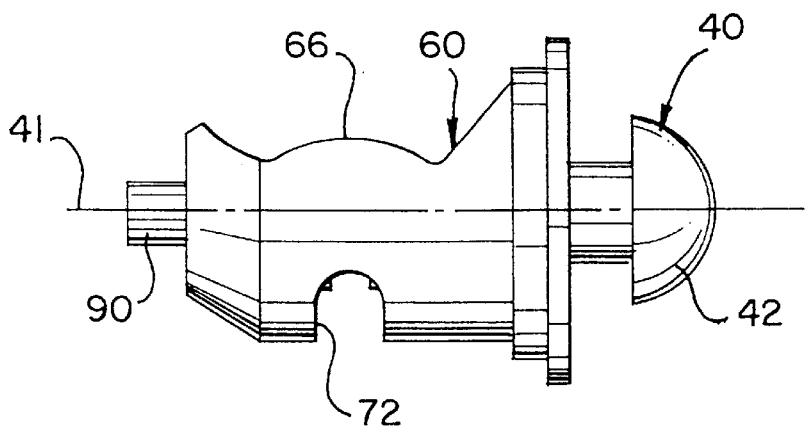
FIG. 7 is an elevational view of a driven shaft formed in accordance with the principles of the present invention.

Driven shaft 40 (which essentially functions as a cam follower), shown in isolation in FIGS. 7–10, has a driven surface 60 along its side (i.e., extending along rotation axis 41 of driven shaft 40). The elevational view of FIG. 7 is similar to the view of driven shaft 40 in FIG. 1, except that driven shaft 40 is shown with driven surface 60 facing upward, rather than downward as in FIG. 1. Typically, driven surface 60 is formed as a cut-away portion of a side of driven shaft 40. Driven surface 60 has alternating hills 62 and valleys 64. Preferably, two hills 62 are provided opposite each other with a valley 64 between adjacent, juxtaposed sides of opposed hills 62, thus spacing hills 62 apart. Viewed another way, the upwardly extending sides of the opposite valleys 64 are joined to form hills 62. Hills 62 and valleys 64 are shaped to conform to the shape of drive surface 50 such that drive surface 50 is in continuous contact with driven surface 60 with substantially no play therebetween as drive shaft 30 rotates during operation of dental tool assembly 10. Specifically, valleys 64 of driven surface 60 are conically cut-away such that conical drive surface 50 may be engaged therewith such that transverse surface portion 56 and distal surface portions adjoining transverse surface portion 56 of conical drive surface 50 are in close contact with the surfaces of a valley 64. Because opposite sides of conical drive surface 50 are at an approximately 90° angle with respect to each other and valleys 64 are shaped to conform to conical drive surface 50 with hills 62 formed at the sides of valleys 64, peaks 66 of hills 62 are preferably also at an approximately 90° angle with respect to each other. The contour of driven surface 60 may be better understood from a review of the elevational views of FIGS. 8 and 10.

The camming action of the present invention, which permits rotation of drive shaft 30 to cause oscillatory rotation of driven shaft 40 as a result of the interaction of the shapes of driving surfaces 50, 60, will now be described. When drive surface 50 engages a valley 64 of driven surface 60, driven shaft 40 is in a rest position (i.e., driven surface 60 completely faces drive surface 50 and proximal end 14 of housing 12, rather than a side of housing 12, as shown in FIG. 1). As drive shaft 30 rotates about rotation axis 31, drive surface 50 moves along driven surface 60 until drive surface 50 engages a hill 62. As described above, and as may be seen in FIG. 8, the peaks 66 of opposite hills 62 are positioned substantially 180° apart with the bottoms 65 of valleys 64 approximately 90° from each peak 66. Thus, when drive surface 50 has rotated 90° from a rest position in contact with valley 64 (such as shown in cross-sectional view 2A), drive surface 50 comes into contact with adjacent hill 62. When transverse surface portion 56 of drive surface 50 contacts peak 66 of an adjacent hill 62, peak 66 is also transverse to rotation axis 31 such that driven shaft 40 is rotated 90° about its rotation axis 41 from its rest position. It is noted that peaks 66 are at an approximately 90° angle with respect to each other, as may be seen in FIG. 2B, and longitudinal and transverse portions 54, 56 of drive surface 50 are also at an approximately 90° angle with respect to each other, as may be appreciated with reference to FIGS. 1, 2B, and 3. Thus, when transverse portion 56 of drive surface 50 contacts a peak 66 to rotate driven shaft 40, longitudinal portion 54 is in contact with the opposite peak 66. As drive surface 50 continues to be rotated upon rotation of drive shaft 30, drive surface 50 contacts the next valley 64 (opposite the first-mentioned valley), returning driven shaft 40 to the rest position. Further rotation of drive shaft 30 brings drive surface 50 into contact with the next hill 62 (opposite the first-mentioned hill), thereby rotating driven shaft 40, in the same manner as described above but in the opposite direction, 90° about rotation axis 41. Thus, driven shaft 40 oscillates a total of 90°, performing a quarter turn in opposite directions from a rest position.

Figure 8:
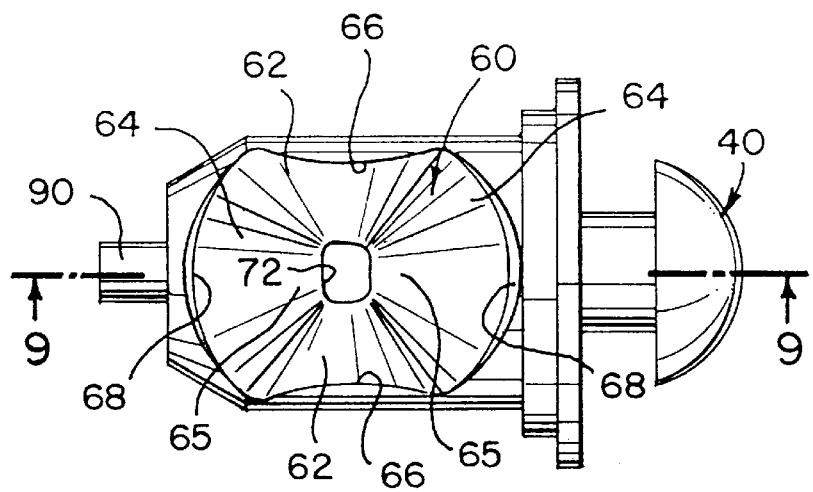
FIG. 8 is a plan view of the driven shaft of FIG. 7.
Figure 9:
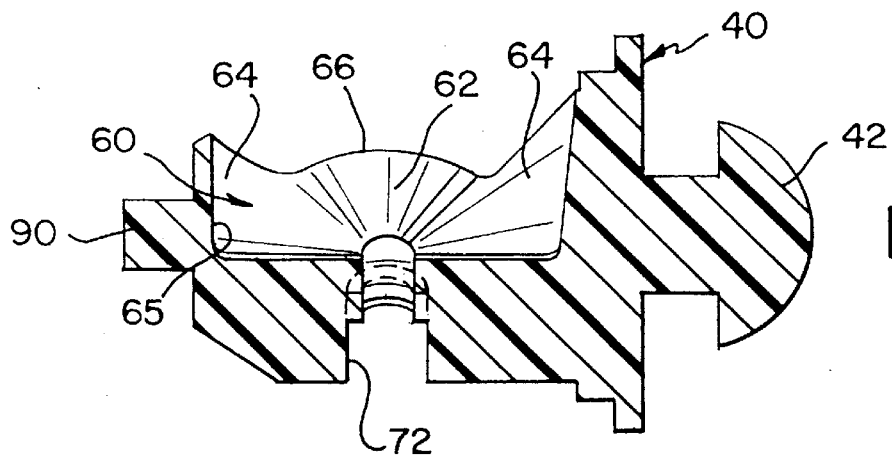
FIG. 9 is a cross-sectional view along line 9—9 of the driven shaft of FIG. 8.
Figure 10:
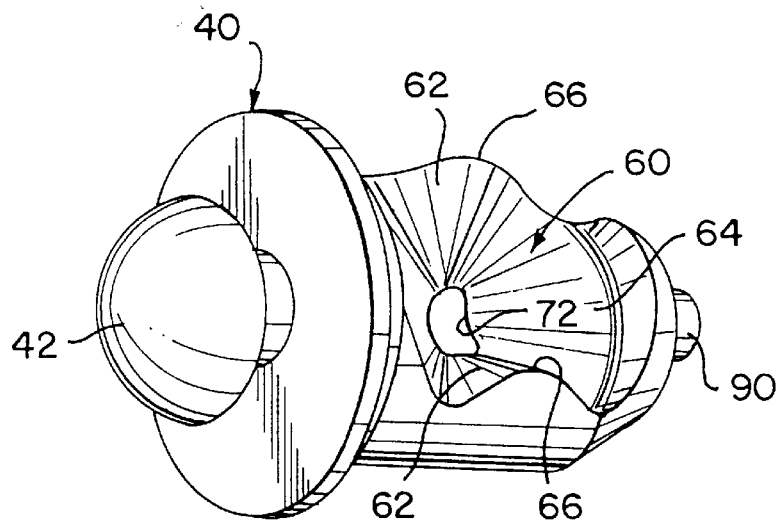
FIG. 10 is a perspective view of the driven shaft of FIGS. 7—9.
Figure 11:
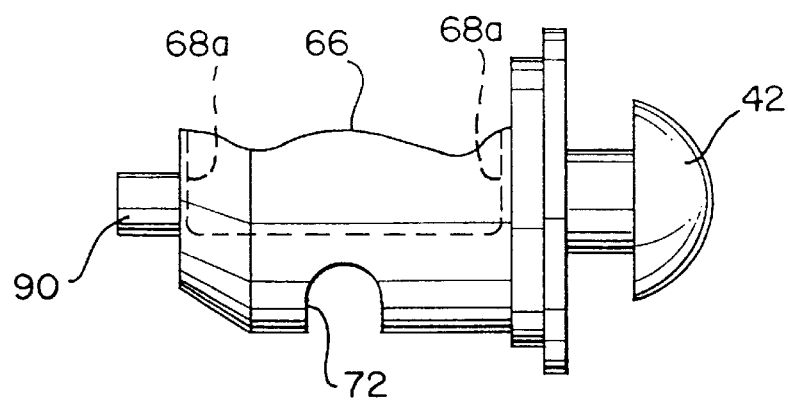
FIG. 11 is an elevational view of a driven shaft similar to that of FIG. 7 but with straight transverse walls of the driven surface.
Figure 12:
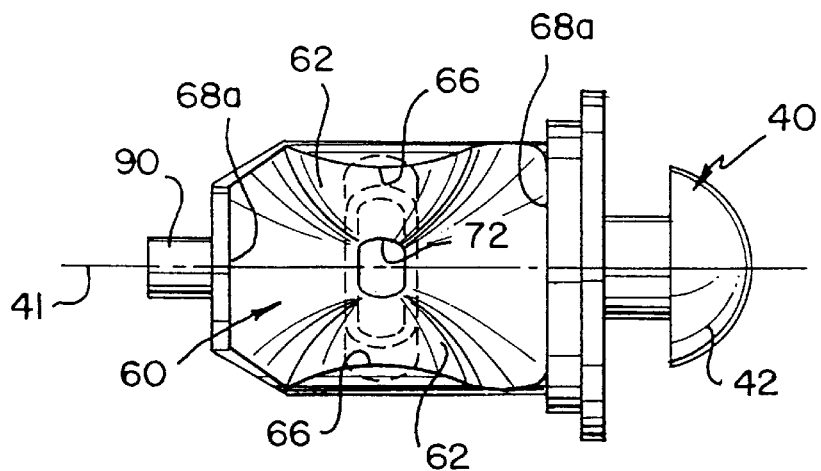
FIG. 12 is a plan view of the driven shaft of FIG. 11.

As may be seen in the plan view of FIG. 8, transverse side walls 68 of driven surface 60 are curved. However, in order to provide greater clearance between side walls 68 and drive shaft 30 (particularly the outer walls of enlarged region 30*a* extending substantially parallel to rotation axis 31) substantially straight side walls 68*a* may, instead, be provided, as shown in FIGS. 11 and 12. Straight side walls 68*a* extend, from the widest portions of valleys 64, along the periphery of driven surface 60 substantially perpendicular to rotation axis 41 of driven shaft 40.

Because typically only oscillatory rotation, without axial reciprocation, of driven shaft 40 is desired, it is desirable to fix drive shaft 30 with respect to driven shaft 40. In accordance with the principles of the present invention, drive shaft 30 is provided with an axially extending pin 70 that is substantially aligned with rotation axis 31. Driven shaft 40 is provided with a corresponding slot 72, which may extend completely through driven shaft 40, as shown in FIGS. 2A, 2B, and 7–10. It will be understood that slot 72 need not extend completely through driven shaft 40, as shown, as long as sufficient engagement between pin 70 and slot 72 is achieved. The axial extent of slot 72 along rotation axis 41 of driven shaft 40 is selected to provide a substantially close fit with the diameter of pin 70 to prevent axial reciprocation of driven shaft 40 along axis 41. However, the transverse extent of slot 72 (in a direction perpendicular to axis 41) is selected such that 90° rotation of driven shaft 40 with respect to drive shaft 30 (45° rotation of driven shaft 40 in each direction from the rest position) is permitted without causing shifting of either shaft 30, 40 from respective axes 23, 25 of housing 12.

In order to prevent movement of shafts 30, 40 from their proper positions within channels 22, 24 of housing 12, position retaining elements are provided as follows. In order to prevent axial shifting of drive shaft 30 along axis 31, drive shaft 30 is provided with at least one radially extending stop flange 80. As shown in FIGS. 1 and 3–5, preferably a proximal flange 82 and a distal flange 84 are provided. Flange 58 may also be considered to perform the same function as that of flanges 82 and 84 and thus may be considered a stop flange 80 as well. Housing 12 is provided with a latch 86 (inserted after assembly in order to maintain the parts of dental tool assembly 10 in place) having a position retaining surface 89 extending radially inwardly from the walls of channel 22. Position retaining surface 89 is positioned adjacent and along a retaining surface 83 of proximal flange 82 to prevent proximal axial movement of drive shaft 30 towards proximal end 14 of housing 12. Additional position retaining surfaces may be provided extending radially inwardly from the inner walls of channels 22 to engage proximal position retaining surfaces on flanges 58 and 84 as well. It will be understood that the position retaining surfaces formed on housing 12 need not be in the form of a latch, but may be in any other form, such as a radially inwardly extending shoulder, that provides a sufficient surface area for engaging a proximal face of at least one of the flanges 80 on drive shaft 30. Moreover, the position retaining surfaces on housing 12 must be securely fixed to housing 12 along axis 23 to prevent movement of drive shaft 30 along axis 23.

In order to secure axial alignment of driven shaft 40 with axis 25, a positioning pin 90 may be provided at a rear, inner end of driven shaft 40 to fit within bore 92 at a rear end of channel 24 of housing 12, as shown in FIG. 1. Pin 90 not only serves to maintain proper alignment of driven shaft 40 during use, but also facilitates alignment of driven shaft 40 in housing 12 during assembly.

Preferably, to assemble dental tool assembly 10, driven shaft 40 is first positioned in housing 12, with pin 90 fitting within bore 92 such that rotation axis 41 of driven shaft 40 is properly aligned with longitudinal axis 25 of channel 24.

Driven shaft 40 is rotated into its rest position such that driven surface 60 faces proximal end 14 of housing 12. Drive shaft 30 may then be inserted into channel 22, with pin 70 extending into slot 72 of driven shaft 40. Latch 86 then is positioned such that position retaining surface 89 faces position retaining surface 83 to maintain drive shaft 30 in its proper position along longitudinal axis 31 of channel 22. Dental tool assembly 10 then is ready for coupling with the desired handpiece.

Preferably, housing 12, drive shaft 30, and driven shaft 40 are formed from a rigid plastic that provides the requisite wear resistance and toughness for a prophy angle, yet is economical and capable of being molded. Most preferably, the elements of assembly 10 are formed from acetal, such as sold under the trademark DELRIN 100 manufactured by E.I. Du Pont deNemours and Company of Delaware. Thus, dental tool assembly 10 is strong, yet economical enough to be disposable. However, it will be understood that the principles of the present invention are applicable to non-disposable dental tool assemblies, formed from, for example, metal, as well. If desired, polypropylene may be used to form at least the housing 12 of the assembly.

While the foregoing description and drawings represent the preferred embodiments of the present invention, it will be understood that various additions, modifications and substitutions may be made without departing from the spirit and scope of the present invention as defined in the accompanying claims. In particular, it will be clear that the present invention may be embodied in other specific forms, structures, arrangements, proportions, and with other elements, materials, and components, without departing from the spirit or essential characteristics thereof. For example, although housing 12 is in the form of a prophy angle, driving mechanism 28 may be used in any other desired dental tool assembly, or any other motorized device that requires oscillating rotary motion of an output end. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A driving mechanism for a dental tool assembly, said driving mechanism comprising:
    a drive shaft having a rotation axis and a drive surface; and
    a driven shaft having a rotation axis and a driven surface; wherein:
        said drive shaft and said driven shaft are positioned with respect to each other such that said rotation axis of said drive shaft is transverse to said rotation axis of said driven shaft and said drive surface and said driven surface are in contact;
        said drive surface and said driven surface cooperate with one another such that rotation of said drive shaft causes reciprocation of said driven shaft about said rotation axis of said driven shaft;
        said drive surface and said driven surface are each curved such that said drive surface and said driven surface are in continuous contact upon rotation of said drive shaft about said rotation axis of said drive shaft;
        said drive surface is substantially conical; and
        said conical drive surface has cone axis that is at an approximately 45° angle with respect to said rotation axis of said drive shaft and transverse surface portion that is at an approximately 90° angle with respect to said rotation axis.

2. A driving mechanism for a dental tool assembly, said driving mechanism comprising:
    a drive shaft having a rotation axis and drive surface; and
    a driven shaft having rotation axis and a driven surface; wherein:
        said shaft and said driven shaft are positioned with respect to each other such that said rotation axis of said drive shaft is transverse to said rotation axis of said driven shaft and said drive surface and driven surface are in contact;
        said drive surface and said driven surface cooperate with one another such that rotation of said drive shaft causes reciprocation of said driven shaft about said rotation axis of said driven shaft;
        said drive surface and said driven surface are each curved such that said drive surface and said driven surface are in continuous contact upon rotation of said drive shaft about said rotation axis of said drive shaft;
        said drive surface is substantially conical; and
        said driven surface has alternating hills and valleys and said valleys are formed with substantially conical surfaces for engaging said control driving surface.

3. A driving mechanism as in claim 2, wherein said alternating hills and valleys include a pair of opposite hills and a pair of opposite valleys, each valley having upwardly extending sides, said hills being formed by adjacent sides of said opposite valleys.

4. A driving mechanism for a dental tool assembly, said driving mechanism comprising:
    a drive shaft having a rotation axis and a drive surface; and
    a driven shaft having a rotation axis and a driven surface;
    wherein said drive shaft and said driven shaft are positioned with respect to each other such that said rotation axis of said drive shaft is transverse to said rotation axis of said driven shaft and said drive surface and said driven surface are in contact;
    said drive surface and said driven surface are each curved such that said drive surface and said driven surface are in continuous contact upon rotation of said drive shaft about said rotation axis of said drive shaft;
    said drive surface is substantially conical;
    said driven surface has alternating hills and valleys;
    said valleys are formed with substantially conical surfaces for engaging said conical driving surface;
    said alternating hills and valleys include a pair of opposite hills and a pair of opposite valleys, each valley having upwardly extending sides, said hills being formed by adjacent sides of said opposite valleys; and
    wherein rotation of said drive shaft causes said drive surface to continuously engage alternating hills and valleys of said driven surface such that upon rotation of said drive shaft said driven shaft is in a rest position when said conical drive surface contacts a first of said pair of valleys, said driven shaft is rotated approximately 45° in a first direction about said rotation axis of said driven shaft when said transverse surface portion of said drive surface contacts a first of said pair of hills, said driven shaft is returned to said rest position when said conical drive surface contacts the second of said pair of valleys opposite said first valley, and said driven shaft is rotated approximately 45° about said rotation axis of said driven shaft in a second direction opposite said first direction when said transverse surface portion of said drive surface contacts the second of said pair of hills opposite said first hill, whereby rotation of said drive shaft causes rotational oscillation of said driven shaft.

5. A driving mechanism for a dental tool assembly, said driving mechanism comprising:

a drive shaft having a rotation axis and drive surface; and a driven shaft having a rotation axis and a driven surface; wherein:

said drive shaft and said driven shaft are positioned with respect to each other such that said rotation axis of said drive shaft is transverse to said rotation axis of said driven shaft and said drive surface and surface and said driven surface are in contact;

said drive surface and said driven surface cooperate with one another such that rotation of said drive shaft causes reciprocation of said driven shaft about said rotation axis of said driven shaft;

said drive surface and said driven surface are each curved such that said drive surface and said driven surface are in continuous contact upon rotation of said drive shaft about said rotation axis of said drive shaft;

said drive shaft included a distal pin extending along said rotation axis of said drive shaft towards said driven shaft; and said driven shaft includes a slot defined therein for receiving said distal pin.

6. A driving mechanism as in claim 5, wherein said slot has a width in an axial direction along said rotation axis of said driven shaft, said width of said slot being selected to provide a substantially close fit with said locking pin to prevent axial reciprocation of said driven shaft along said rotation axis of said driven shaft.

7. A disposable dental tool assembly comprising:

a housing having a longitudinal channel and a transverse channel defined therein, said longitudinal channel and said transverse channel being transverse with respect to each other;

a drive shaft having a rotation axis and a drive surface, said drive shaft being positioned within said longitudinal channel; and a driven shaft having a rotation axis and a driven surface, said driven shaft being positioned within said transverse channel; wherein said drive shaft and driven shaft are positioned with respect to each other such that said drive surface and said driven surface are in contact;

said drive surface and said driven surface cooperate with one another such that rotation of said drive shaft causes reciprocation of said driven shaft about said rotation axis of said driven shaft;

said drive surface and said driven surface are each curved such that said drive surface and said driven surface are in continuous contact upon rotation of said drive shaft about said rotation axis of said drive shaft; and said drive surface is substantially conical and has a cone axis that is at an approximately 45° angle with respect to said rotation axis of said drive shaft and a transverse surface portion that is approximately 90° angle with respect to said axis.

8. A disposable dental tool assembly as in claim 7, wherein:

said surface has alternating hills and valleys;

said valleys have substantially conical surfaces for engaging said conical driving surface;

said valleys include a pair of opposite valleys, each valley having upwardly extending sides; and said hills are formed by adjacent sides of said opposite valleys.

9. A disposable dental tool assembly as in claim 8, wherein rotation of said drive shaft causes said drive surface to continuously engage alternating hills and valleys of said driven surface such that said driven shaft is in a rest position when said conical drive surface contacts a valley, and said driven shaft is rotated approximately 45° about said rotation axis of said driven shaft when said transverse surface portion of said drive surface contacts a hill.

10. A disposable dental tool assembly comprising:

a housing having a longitudinal channel and a transverse channel defined therein, said longitudinal channel and said transverse channel being transverse with respect to each other;

a drive shaft having a rotation axis and a drive surface, said drive shaft being positioned within said longitudinal channel; and a driven shaft having a rotation axis and driven a surface, said driven shaft being positioned within said transverse channel; wherein:

said drive shaft and driven shaft are positioned with respect to each other such that said drive surface and said driven surface are in contact;

said drive surface and said driven surface cooperate with one another such that rotation of said drive shaft causes reciprocation of said driven shaft about said rotation axis of said driven shaft;

said drive surface and said driven surface are each curved such that said drive surface and said driven surface are in continuous contact upon rotation of said drive shaft about said rotation axis of said drive shaft;

said drive shaft includes a distal pin extending along said rotation axis of said drive shaft towards said driven shaft;

said driven shaft includes a slot defined therein for receiving said distal pin; and said slot has an axial extent along said rotation axis of said driven shaft selected to provide a substantially close fit with said locking pin to prevent axial reciprocation of said driven shaft along said rotation axis of said driven shaft.

* * * * *